(12) United States Patent
Dolitzky et al.

(10) Patent No.: US 7,361,756 B2
(45) Date of Patent: Apr. 22, 2008

(54) METHOD OF MAKING 7-(4-BROMOBUTOXY)-3,4-DIHYDROCARBOSTYRIL

(75) Inventors: Ben-Zion Dolitzky, Petach Tiqva (IL); Jean Hildesheim, Mazkeret Batya (IL); Alisa Berlin, Jerusalem (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 363 days.

(21) Appl. No.: 11/053,072

(22) Filed: Feb. 7, 2005

(65) Prior Publication Data

US 2005/0215585 A1   Sep. 29, 2005

Related U.S. Application Data

(60) Provisional application No. 60/542,412, filed on Feb. 5, 2004.

(51) Int. Cl.
*C07D 265/00* (2006.01)
*C07D 215/38* (2006.01)

(52) U.S. Cl. .......................... 544/63; 546/158
(58) Field of Classification Search ............... 544/63; 546/158
See application file for complete search history.

(56) References Cited

U.S. PATENT DOCUMENTS

| 5,006,528 A | 4/1991 | Oshiro et al. |
| 6,630,590 B1 | 10/2003 | Aki et al. |
| 2006/0079689 A1* | 4/2006 | Naddaka et al. ............ 544/363 |

FOREIGN PATENT DOCUMENTS

| EP | 0 367 141 A | 5/1990 |
| JP | 02191256 | 7/1990 |
| WO | WO 02/14283 A | 2/2002 |
| WO | WO 03/026659 | 4/2003 |
| WO | WO 04/083183 A | 9/2004 |
| WO | WO 04/106322 A | 12/2004 |
| WO | WO 05/09990 A1 | 2/2005 |

OTHER PUBLICATIONS

Aoki, et al. "Study on Crystal Transformation of Aripiprazol", *The Fourth Japan-Korea Symposium On Separation Technology*, 1996, 937-940.
U.S. Publication No. 2003/176703, Publication date: Sep. 18, 2003, Mendelovici, et al.
Oshiro Yasuo, et al. "Novel Antipsychotic Agents with Dopamine Autoreceptor Agonist Properties: Synthesis and Pharmacology of 7-'4-(4-Phenyl-1-piperaziny 1) butoxy-3,4-dihydro-2(1H)-quinolinone Derivatives", J. of Med. Chem., vol. 41, 1998, 658-667.
Banno K et al, "Studies on 2 (1H)-Quinolinone Derivatives as Neuroleptic Agents. I. Synthesis and Biological Activities of (4-Phenyl-1-Piperazinyl)-Propoxy-2 (1H)-Quinolinone Derivatives", Chemical And Pharmaceutical Bulletin, vol. 36, No. 11, pp. 4377-4388 (1988).

* cited by examiner

*Primary Examiner*—D. Margaret Seaman
(74) *Attorney, Agent, or Firm*—Kenyon & Kenyon LLP

(57) ABSTRACT

The invention encompasses synthesizing 7-(4-bromobutoxy)-3,4-dihydrocarbostyril by mixing 7-hydroxy-tetrahydroquinolinone, dibromobutane, and at least one base to form a reaction mixture; heating the reaction mixture; cooling the reaction mixture; and isolating the 7-(4-bromobutoxy)-3,4-dihydrocarbostyril from the reaction mixture. The invention also encompasses using phase transfer catalysts during the reaction.

26 Claims, No Drawings

… (US 7,361,756 B2)

METHOD OF MAKING 7-(4-BROMOBUTOXY)-3,4-DIHYDROCARBOSTYRIL

RELATED US APPLICATION DATA

This application claims the benefit of U.S. provisional application No. 60/542,412, filed Feb. 5, 2004.

FIELD OF THE INVENTION

The present invention is directed to processes for making 7-(4-bromobutoxy)-3,4-dihydrocarbostyril (BBQ), an intermediate in the synthesis of aripiprazole under neat conditions, using phase transfer catalysts, or using a low boiling point solvent

BACKGROUND OF THE INVENTION

Schizophrenia is the most common type of psychosis caused by an excessive neurotransmission activity of the dopaminergic nervous system in the central nervous system. A number of drugs have been developed having the activity to block the neurotransmission of dopaminergic receptor in the central nervous system. For example, among the drugs developed are phenothiazine-type compounds such as chlorpromazine; butyrophenone-type compounds such as haloperidol; and benzamide-type compounds such as sulpiride. The drugs are used to improve so-called positive symptoms in the acute period of schizophrenia such as hallucinations, delusions, excitations, and the like. Many drugs for treating schizophrenia, however, are not effective for improving the so-called negative symptoms which are observed in the chronic period of schizophrenia such as apathy, emotional depression, hypopsychosis, and the like. The drugs currently used have produced undesired side effects such as akathisia, dystonia, Parkinsonism dyskinesia, and late dyskinesia, which are caused by blocking the neurotransmission of dopaminergic receptor in the striate body.

Aripiprazole is a pyschotropic drug that exhibits high affinity for dopamine $D_2$ and $D_3$, serotonin $5\text{-HT}_{1A}$ and $5\text{-HT}_{2A}$ receptors, moderate affinity for dopamine $D_4$, serotonin $5\text{-HT}_{2C}$ and $5\text{-HT}_7$, $\alpha_1$-adrenergic and histamine $H_1$ receptors, and moderate affinity for the serotonin reuptake site. Also, aripiprazole has no appreciable affinity for cholinergic muscarinic receptors. The mechanism of action of aripiprazole, as with other drugs having efficacy in schizophrenia, is unknown. It has been proposed, however, that the efficacy of aripiprazole is mediated through a combination of partial agonist activity at $D_2$ and $5\text{-HT}_{1A}$ receptors and antagonist activity at $5\text{-HT}_{2A}$ receptors. Drugs effective for improving the negative symptoms and effective for improving the positive symptoms of schizophrenia are still highly desirable, more so, when the drugs can diminish the undesirable side effects.

U.S. Pat. No. 5,006,528 provides a process for the preparation of BBQ in water in basic conditions. Water can often be difficult to remove from reaction mixtures. Accordingly, the present invention encompasses methods of synthesizing BBQ, an intermediate commonly used in the synthesis of aripiprazole, as aripiprazole is safer than other anti-psychotic drugs such as olanzapine or ziprazidone.

SUMMARY OF THE INVENTION

The invention encompasses processes for preparing 7-(4-bromobutoxy)-3,4-dihydrocarbostyril (BBQ). One embodiment of the invention encompasses synthesizing 7-(4-bromobutoxy)-3,4-dihydrocarbostyril (BBQ) under neat conditions by a process that comprises combining 7-hydroxy-tetrahydroquinolinone (THQ), dibromobutane (DBB), and at least one base to form a reaction mixture; heating the reaction mixture to a suitable temperature and sufficient time to effect the reaction; and isolating the BBQ. Alternatively, a salt of THQ may be used without the need for a base.

When using a salt of THQ, it may be prepared and isolated prior to the synthesis of BBQ or prepared as the first step of a synthetic sequence of BBQ. The THQ salt is typically prepared by reacting THQ and at least one base in an organic solvent until the THQ is completely neutralized; and isolating the THQ salt by the removal of the solvent.

Another embodiment encompasses synthesizing BBQ by a process comprising combining DBB with THQ in organic solvent and at least one base to form a reaction mixture; heating the reaction mixture to a suitable temperature and for a suitable time to effect a reaction; and isolating BBQ. Alternatively, a salt of THQ may be used, alleviating the need for a base. The organic solvent is preferably a low boiling point solvent.

Another embodiment of the invention encompasses synthesizing BBQ using phase transfer catalysts (PTC). Typically, the process comprises combining THQ, DBB, at least one water immiscible organic solvent, at least one base and at least one phase transfer catalyst to form a reaction mixture; heating the reaction mixture to a suitable temperature and for a time sufficient to effect the reaction; and isolating the BBQ. The process may further comprise adding water to the reaction mixture. Alternatively, a salt of THQ may be used, alleviating the need for a base.

DETAILED DESCRIPTION OF THE INVENTION

The present invention encompasses improved syntheses of 7-(4-bromobutoxy)-3,4-dihydrocarbostyril (BBQ) by reacting 7-hydroxy-tetrahydroquinolinone (THQ) under reaction conditions to improve reaction yields and ease of purification. In particular, the invention is directed to the synthesis of BBQ under neat reaction conditions, using phase transfer catalysts, or using at least one low boiling point solvent wherein a purification step is unnecessary.

U.S. Publication No. 2003/176703 discloses the preparation of THQ, and is hereby incorporated by reference.

Typically, under neat reaction conditions BBQ is synthesized without adding any solvent to the reagents, it is only until the work-up phase, i.e., after the reaction has taken place, that solvents are added to the reaction mixture. The process of synthesizing BBQ under neat conditions comprises combining THQ, DBB, and at least one base to form a reaction mixture and heating the reaction mixture to a suitable temperature and for a suitable time to effect the reaction; and isolating BBQ.

DBB should be added in sufficient amount to react with THQ. Preferably, the ratio of THQ to DBB is about 1:1 to about 1:10 mol equivalents of THQ to DBB. Typically, the reaction temperature is from about 50° C. to about 140° C. Preferably, the reaction temperature is from about 130° C. to about 140° C., and more preferably, the reaction temperature under neat reaction conditions is about 140° C. The reaction time should be sufficient to complete the reaction which may depend on scale and mixing procedures, as is commonly known to one skilled in the art. Typically, the reaction time is from about 45 minutes to 10 hours. Preferably, the base is $K_2CO_3$, NaOH, or KOH. Alternatively, a salt of THQ may be used in the process without the need for a base.

Yet another embodiment of the invention encompasses the synthesis of BBQ by mixing DBB with at least one organic solvent, preferably a low boiling point organic solvent, at least one base and THQ to form a reaction mixture; heating the reaction mixture to a suitable temperature and for a suitable time to effect a reaction; and isolating the BBQ. Preferably, the ratio of THQ to DBB is about 1:1 to about 1:10 mol equivalents of THQ to DBB. Preferably the low boiling point organic solvent is selected from the group consisting of ethanol, toluene, heptane, dimethylformamide (DMF), dimethyl sulfoxide (DMSO) and acetonitrile. Typically, the reaction temperature is from about 50° C. to about 140° C. Preferably, the reaction temperature is about 80° C.

The reaction time should be sufficient to complete the reaction which may depend on scale and mixing procedures, as is commonly known to one skilled in the art. Typically, the reaction time is from about 45 minutes to 10 hours. Preferably the reaction time is about 140 minutes. Alternatively, a salt of THQ may be used without the need for a base.

Yet another embodiment of the invention encompasses the preparation of BBQ using phase transfer catalysts (PTC). Typically, the process comprises combining THQ, BBQ, at least one base, at least one water immiscible organic solvent, and at least one phase transfer catalyst to form a reaction mixture; heating the reaction mixture to a suitable temperature for a time sufficient to effect the reaction; and isolating BBQ. The process may further comprise adding water to the reaction mixture. Alternatively, a salt of THQ may be used without the need for a base.

The amount of DBB should be sufficient to react with THQ. Preferably, the amount should be about 1:1 to about 1:5 mol equivalents of THQ to BBQ, and more preferably is about 1 to about 3 mol equivalents. One of ordinary skill in the art can easily determine an appropriate water immiscible solvent. Water immiscible solvents include, but are not limited to, toluene, heptane, or hexane. Typically, the reaction temperature is from about 50° C. to about 140° C. The reaction time should be sufficient to complete the reaction which may depend on scale and mixing procedures, as is commonly known to one skilled in the art. Typically, the reaction time is from about 45 minutes to 10 hours.

Typically, when compounds are reacted, the reactants may be dissolved in a first solvent, such as the water immiscible solvent, and then water is added. In the reaction of the present invention, the water immiscible solvent and water form a two-phase system. Because the reaction may occur at the interface between the two phases, the rate of such an interfacial reaction may be greatly increased by use of a phase transfer catalyst (PTC).

Several classes of compounds are known to be capable of acting as phase transfer catalysts, for example quaternary ammonium compounds and phosphonium compounds, to mention just two. Phase transfer catalysts include, but are not limited to, tetrabutylammonium bromide; tetrabutylammonium hydroxide; TEBA; tricaprylylmethylammonium chloride, such as Aliquat® 336 (manufactured by Aldrich Chemical Company, Inc. Milwaukee, Wis.); dodecyl sulfate, sodium salt; tetrabutylammonium hydrogensulfate; hexadecyl tributyl phosphonium bromide; or hexadecyl trimethyl ammonium bromide. Preferably, the phase transfer catalysts include hexadecyl tributyl phosphonium bromide or hexadecyl trimethyl ammonium bromide. Typically, the phase transfer catalyst is present in an amount of about 0.1 to about 5 mol equivalents to the THQ.

When using a salt of THQ, it may be prepared and isolated prior to the synthesis of BBQ or prepared as the first step of a synthetic sequence of BBQ. The THQ salt is typically prepared by reacting THQ and at least one base in an organic solvent until the THQ is completely neutralized; and isolating the THQ salt by the removal of the solvent. The organic solvent is selected from the group consisting of ethanol, isopropanol, butanol, methanol, THF and acetonitrile. One of ordinary skill in the art with little or no experimentation can easily determine when the THQ is completely neutralized and the method for removing the solvent. Typical bases include, but are not limited to, NaOH, KOH, $Ca(OH)_2$, $Na_2CO_3$, $K_2CO_3$ or $NaHCO_3$. The base is added in a stoichiometric amount to the THQ. Preferably, one equivalent of base is added to one equivalent of THQ. Generally, the reaction temperature is about 50° C.

The isolation of the BBQ obtained by the processes described above comprises cooling the reaction mixture to room temperature and working up the reaction mixture. Working up the reaction mixture comprises adding to the reaction mixture at least one organic solvent and at least one basic aqueous solution; extracting the product using at least one organic solvent; collecting the extracts; drying the extracts; and reducing the volume of the extracts to obtain BBQ. Sufficient aqueous basic solution should be added to the reaction mixture to neutralize any unreacted THQ. Typical bases used in the work up include, but are not limited to, NaOH, KOH, $Ca(OH)_2$, $Na_2CO_3$, $K_2CO_3$ or $NaHCO_3$. Preferably, the base is NaOH, KOH or $K_2CO_3$.

The reaction mixture is extracted with an organic solvent, including, but not limited to, dichloromethane, dichloroethane, butyl acetate, isobutyl acetate, ethyl acetate, t-butyl acetate, MTBE, THF, chlorobenzene or 1,1,2,2-tetrabromoethane (TBE). Thereafter, the organic extracts are collected, dried, and the solvent removed by evaporation using techniques commonly known to one of ordinary skill in the art.

Optionally, BBQ obtained from the above processes may be crystallized. Typically, BBQ is crystallized from at least one suitable organic solvent, such as ethanol or hexane. Preferably, BBQ is recrystallized from an ethanol and hexane mixture.

BBQ prepared according to the above described processes can be used in the preparation of aripiprazole, for example according to U.S. Pat. No. 5,006,528 and according to the commonly assigned U.S. Application No. 11/050,953, filed Feb. 7, 2005, hereby incorporated by reference.

Having described the invention with reference to certain preferred embodiments, other embodiments will become apparent to one skilled in the art from consideration of the specification. The invention is further defined by reference to the following examples describing in detail the process of the invention. It will be apparent to those skilled in the art that many modifications, both to materials and methods, may be practiced without departing from the scope of the invention.

EXAMPLES

HPLC analysis was performed as follows:

A 20 µl sample of BBQ (0.4-0.5 mg/ml) in diluent was injected into a XTerra RP 18 column (250 mm×4.6 mm, 5 µm particle size). The column temperature was 30° C. The eluting was a mixture of eluent A (water and trifluoroacetic acid, pH 3.0) and eluent B (1000 ml acetonitrile to 100 ml trifluoroacetic acid) according to the following profile:

| Flow rate [ml/min] | Time [min] | Eluent A [v/v %] | Eluent B [v/v %] |
|---|---|---|---|
| 1.0 | 0.0 | 70 | 30 |
| 1.0 | 5 | 70 | 30 |
| 1.0 | 15 | 20 | 80 |
| 1.0 | 22 | 20 | 80 |
| 1.0 | 23 | 0 | 100 |
| 1.0 | 25 | 0 | 100 |
| 1.0 | 26 | 0 | 100 |

The column was ran for five minutes past the last data point. A 254 nm wavelength UV detector was used.

Comparative Example 1

Synthesis of BBQ 7-hydroxy-tetrahydroquinolinone (THQ, 1.6 g, 10 mmol), 1,4-dibromobutane (DBB, 21.6 g, 100 mmol), $K_2CO_3$ (5.5 g, 39.8 mmol) in water (60 ml) were heated to reflux for 3.5 hrs while stirring. Thereafter, the reaction mixture was cooled to room temperature (about 25° C.), extracted with dichloromethane (2×60 ml), dried over anhydrous $Na_2SO_4$ and the solvents were removed by evaporation. The final product was identified as BBQ, analyzed by HPLC, and found to have 21% 7-(4-bromobutoxy)-3,4-dihydrocarbostyril in a crude yield of 34.5%.

Example 1

Neat Synthesis of BBQ 7-hydroxy-tetrahydroquinolinone (THQ, 1.6 g, 10 mmol), dibromobutane (DBB, 100 mmol, 12 ml), $K_2CO_3$ (11 mmol) were heated to 140° C. for 4 hrs while stirring, after which the reaction mixture was cooled to room temperature (about 25° C.). Dichloromethane and water containing an excess of NaOH (50-200% molarity) were added to the cooled mixture. The mixture was extracted with dichloromethane. Thereafter, the organic phase was separated, dried with sodium sulfate, and the solvent was removed by evaporation until a solid residue was left. The solid residue was triturated with hexane (3×5 ml) to remove the last traces of DBB. The solid was recrystallized from a ethanol/hexane mixture to give BBQ in 60% yield.

Example 2

Neat Preparation of 7-(4-bromobutoxy)-3,4-dihydrocarbostyril (BBQ) with THK Potassium Salts Equivalent mols of 7-hydroxy-tetrahydroquinoline (THQ) and KOH were allowed to react in absolute ethanol until the THQ was completely neutralized. The ethanol was removed by evaporation and the remaining THQ potassium salt (THQK salt) was dried.

THQK salt (1 g, 5 mmol, 1 eq.) and dibromobutane (6 ml, 50 mmol, 10 eq.) were heated to 140° C. while stirring and kept at this temperature for 1.5 hrs. Dichloromethane (20 ml) and water (20 ml) were added to the reaction mixture; thereafter, after the solution had cooled to room temperature, an excess of NaOH (5%) solution was added. The mixture was extracted with dichloromethane. Thereafter, the organic phase was separated, dried with sodium sulfate, and the solvent was removed by evaporation to afford mostly clean BBQ as a solid in 60% yield, with purity of 70%.

Example 3

Preparation of BBQ in Acetonitrile

THQK salt (1 g, 5 mmol) in acetonitrile (15 ml) and dibromobutane (0.6 ml, 5 mmol, 1 eq.) were refluxed at 81° C. for 140 min while stirring. The solvent was removed by evaporation and the remainder was extracted with an ethylacetate and water mixture (60 ml, 1:1) containing a slight excess of NaOH (5%). The reaction mixture was extracted with ethyl acetate, and the organic phase was separated, dried over sodium sulfate, and the solvent removed by evaporation. A solid was obtained (0.9 g, 62% yield), with 64% purity.

Example 4

Preparation of BBQ in Acetonitrile using Phase Transfer Catalysts

THQ (1.6 g, 10 mmol, 1 eq.), DBB (3.6 ml, 30 mmol, 3 eq.), $K_2CO_3$ (1.7 g, 12 mmol, 1.2 eq), and hexadecyl tributyl phosphonium bromide (1.02 g, 2 mmol, 0.2 eq) in acetonitrile (25 ml) were refluxed while stirring. After 60 min, the solvent was removed by evaporation and the remainder was extracted with a mixture of ethyl acetate (20 ml) and water containing an excess of NaOH (10 ml). The organic layer was separated, dried over sodium sulfate, filtered, and the solvent was removed by evaporation. The reaction provided 1 g of a product free of starting material THQ in a 67% yield, and with a purity of 81.5%.

Example 5

Preparation of BBQ in Toluene/Water with Hexadecyl Tributyl Phosphonium Bromide

THQK salt (1 g, 5 mmol, 1 eq.), DBB (0.6 ml, 5 mmol, 5 eq.), toluene (5 ml), water (5 ml), and hexadecyl tributyl phosphonium bromide (0.5 g, 1 mmol, 0.2 eq.) were heated to a gentle reflux. After 3.5 hrs at reflux, the crude reaction mixture was filtered. The organic phase was dried over sodium sulfate, filtered, and the solvent removed by evaporation to yield 0.9 g or 60% of BBQ, with a purity of 82.5%.

Example 6

Preparation of BBQ in Toluene/Water with Hexadecyl Trimethyl Ammonium Bromide

THQ (1.6 g, 10 mmol, 1 eq.), DBB (3.6 ml, 30 mmol, 3 eq.), $K_2CO_3$ (1.7 g, 12 mmol, 1.2 eq), toluene (8 ml), water (8 ml), and hexadecyl trimethyl ammonium bromide (0.73 g, 2 mmol, 0.2 eq) were heated to reflux. After 1.5 hr, the reaction mixture was filtered, and a mixture of toluene and water containing a slight excess of NaOH was added. The organic layer was separated, dried over sodium sulfate, filtered, and solvent was removed by evaporation. The reaction provided 1.8 g of BBQ (60%), with a purity of 87.5%.

Example 7

Preparation of BBQ in Toluene/Water with Hexadecyl Tributyl Phosphonium Bromide THQ (1.6 g, 10 mmol, 1 eq.), DBB (3.6 ml, 30 mmol, 3 eq.), $K_2CO_3$ (1.7 g, 12 mmol, 1.2 eq.), toluene (8 ml), water (8 ml), and hexadecyl tributyl phosphonium bromide (1.02 g, 2 mmol, 0.2 eq.) were heated to reflux. After 1 hr, the reaction mixture was filtered, and a mixture of toluene and water containing a slight excess of NaOH was added. The organic layer was separated, dried over sodium sulfate, filtered, and solvent was removed by evaporation. The reaction provided 2 g of a solid, recrystallized from hot cyclohexane (40 ml) to yield 1.5 g of BBQ in a 50% yield and with a purity of 85.5%.

What is claimed is:

1. A process for synthesizing 7-(4-bromobutoxy)-3,4-dihydrocarbostyril comprising:
    combining 7-hydroxy-tetrahydroquinolinone or a salt thereof and dibromobutane to form a reaction mixture;
    heating the reaction mixture to a temperature of about 50° C. to 140° C.; and
    isolating the 7-(4-bromobutoxy)-3,4-dihydrocarbostyril from the reaction mixture.

2. The process of claim 1, further comprising adding at least one base to the reaction mixture.

3. The process according to claim 2, wherein the base is selected from the group consisting of $K_2CO_3$, NaOH, and KOH.

4. The process according to claim 1, wherein 7-hydroxy-tetrahydroquinolinone or a salt thereof and dibromobutane are present in a mol ratio of about 1:1 to about 1:10.

5. The process according to claim 1, wherein the temperature is about 130° C. to about 140° C.

6. The process according to claim 1, wherein the salt of 7-hydroxy-tetrahydroquinolinone is prepared by reacting 7-hydroxy-tetrahydroquinolinone and at least one base in an organic solvent until the 7-hydroxy-tetrahydroquinolinone is completely neutralized; and isolating the 7-hydroxy-tetrahydroquinolinone salt by removal of the solvent.

7. The process according to claim 6, wherein the organic solvent is ethanol, isopropanol, butanol, methanol, THF, acetonitrile, or a mixture thereof.

8. A process for synthesizing 7-(4-bromobutoxy)-3,4-dihydrocarbostyril comprising:
    combining 7-hydroxy-tetrahydroquinolinone or a salt thereof, dibromobutane, and
    at least one organic solvent to form a reaction mixture;
    heating the reaction mixture to a temperature of about 50° C. to about 140° C.; and
    isolating the 7-(4-bromobutoxy)-3,4-dihydrocarbostyril from the reaction mixture.

9. The process of claim 8, wherein the organic solvent is a low boiling point organic solvent.

10. The process of claim 9, wherein the low boiling point organic solvent is selected from the group consisting of ethanol, toluene, heptane, dimethylformamide (DMF), dimethyl sulfoxide (DMSO), and acetonitrile.

11. The process of claim 8, further comprising adding at least one base to the reaction mixture.

12. The process according to claim 11, wherein the base is selected from the group consisting of $K_2CO_3$, NaOH, and KOH.

13. The process according to claim 8, wherein 7-hydroxy-tetrahydroquinolinone and dibromobutane are present in a mol ratio of about 1:1 to about 1:10.

14. The process according to claim 8, wherein the temperature is about 130° C. to about 140° C.

15. The process according to claim 8, wherein the salt of 7-hydroxy-tetrahydroquinolinone salt is prepared by reacting 7-hydroxy-tetrahydroquinolinone and at least one base in an organic solvent until the 7-hydroxy-tetrahydroquinolinone is completely neutralized; and isolating the 7-hydroxy-tetrahydroquinolinone salt by removal of the solvent.

16. The process according to claim 15, wherein the organic solvent is ethanol, acetonitrile, isopropanol, butanol, methanol, THF, or a mixture thereof.

17. A process for synthesizing 7-(4-bromobutoxy)-3,4-dihydrocarbostyril comprising:
    combining 7-hydroxy-tetrahydroquinolinone or salt thereof, dibromobutane, at least one water immiscible organic solvent and at least one phase transfer catalyst to form a reaction mixture;
    heating the reaction mixture to a temperature of about 50° C. to about 140° C.; and
    isolating the 7-(4-bromobutoxy)-3,4-dihydrocarbostyril.

18. The process of claim 17, further comprising adding at least one base.

19. The process according to claim 18, wherein the base is selected from the group consisting of $K_2CO_3$, NaOH, and KOH.

20. The process of claim 17, wherein the reaction further comprises adding water.

21. The process according to claim 17, wherein the phase transfer catalyst is tetrabutylammonium bromide; tetrabutylammonium hydroxide; TEBA; tricaprylylmethylammonium chloride; dodecyl sulfate, sodium salt; tetrabutylammonium hydrogensulfate; hexadecyl tributyl phosphonium bromide; or hexadecyl trimethyl ammonium bromide.

22. The process according to claim 17, wherein the phase transfer catalyst is present in a molar ratio of about 0.1 to 5 mol per mol of 7-hydroxy-tetrahydroquinolinone.

23. The process according to claim 17 wherein the 7-hydroxy-tetrahydroquinolinone and the dibromobutane are present in a molar ratio of 1:1 to about 1:5.

24. The process according to any one of claims 1, 8, and 17, further comprising crystallizing the 7-(4-bromobutoxy)-3,4-dihydrocarbostyril.

25. The process according to claim 24, wherein the 7-(4-bromobutoxy)-3,4-dihydrocarbostyril is crystallized from ethanol, hexane, or a combination thereof.

26. The process of any one of claims 1, 8, and 17, further comprising converting the 7-(4-bromobutoxy)-3,4-dihydrocarbostyril with a base and an organic solvent to make aripiprazole.

* * * * *